US011872031B2

United States Patent
Arab et al.

(10) Patent No.: US 11,872,031 B2
(45) Date of Patent: Jan. 16, 2024

(54) ELECTRICAL TRANSTYMPANIC STIMULATOR

(71) Applicants: Maryam Banimostafa Arab, Tehran (IR); Hamed Sadjedi, Tehran (IR); Samira Kooshkestani, Tehran (IR); Hesamaldin Emamdjomeh, Tehran (IR)

(72) Inventors: Maryam Banimostafa Arab, Tehran (IR); Hamed Sadjedi, Tehran (IR); Samira Kooshkestani, Tehran (IR); Hesamaldin Emamdjomeh, Tehran (IR)

( * ) Notice: Subject to any disclaimer, the term of this patent is extended or adjusted under 35 U.S.C. 154(b) by 286 days.

(21) Appl. No.: 16/879,807

(22) Filed: May 21, 2020

(65) Prior Publication Data
US 2021/0361194 A1   Nov. 25, 2021

(51) Int. Cl.
*A61N 1/36* (2006.01)
*A61B 5/12* (2006.01)
*A61N 1/04* (2006.01)

(52) U.S. Cl.
CPC ............ *A61B 5/126* (2013.01); *A61N 1/0456* (2013.01); *A61N 1/3603* (2017.08); *A61N 1/36036* (2017.08)

(58) Field of Classification Search
CPC ............ A61N 1/36036; A61N 1/36038; A61N 1/36039
See application file for complete search history.

(56) References Cited

U.S. PATENT DOCUMENTS

2020/0338349 A1* 10/2020 Djalilian .............. A61N 5/0622

* cited by examiner

*Primary Examiner* — George R Evanisko

(57) ABSTRACT

An electrical transtympanic stimulator for auditory processing evaluation is disclosed. The stimulator comprises a processor, a digital-to-analog converter, a voltage-to-current convertor, and one or more electrodes. The digital-to-analog converter in communication with the processor and power source is configured to convert digital signals into analogue voltage signals. The voltage-to-current convertor in communication with the digital-to-analog converter via an amplifier is configured to convert the analogue voltage signals to current signals/pulses that are proportional to the analogue voltage signals. The electrodes in communication with the voltage-to-current convertor, configured to locate in the ear canal and on the skin around the skull of a patient, thereby performing the auditory processing evaluation by applying the current pulses to the ear canal and skull in different waveforms at various frequency ranges with parameters. The protection circuit configured to disconnect the power supply to the electrodes if the current value exceeds a threshold value.

14 Claims, 14 Drawing Sheets

| RL | 1K | 2.2K | 5.6K | 8.6K | 10K | 12K | |
|---|---|---|---|---|---|---|---|
| IL (Simulated) | 500 | 500 | 500 | 500 | 500 | 491 | 491 |
| IL (Pratical Results) | 490 | 490 | 490 | 490 | 482 | 481 | 479 |

ELECTRICAL TRANSTYMPANIC STIMULATOR

BACKGROUND OF THE INVENTION

Hearing loss is caused by dysfunction of the inner ear, the cochlea, and auditory nerve. This kind of hearing losses are normally due to damaged hair cells in the cochlea. The hearing loss may be due to many causes, but most result in hearing loss that is conductive or sensorineural hearing losses. The conductive hearing loss (CHL) is a hearing problem that occurs when the passage of sound is blocked in either the ear canal or in the middle ear. The conductive hearing loss is usually between 25 and 65 dB and is ranked as mild to moderate. People with conductive hearing impairment find it difficult to hear quiet sounds well, but are able to hear clearly when sound is amplified.

Sensorineural hearing loss is caused by the loss of sensory cells (hair cells) in the cochlea or due to a damage to these cells and is considered as a permanent loss. The sensorineural hearing loss could be mild, moderate, severe, or profound. Mild to profound sensorineural hearing loss could be treated by means of middle ear hearing devices or implants. In many healthcare systems, electrical stimulation of the human auditory system using cochlear implants, is a common treatment for severe to profound deafness. Cochlear implants perform natural energy conversion by directly stimulating the auditory nerve with electrical pulses. Cochlear implants, therefore, somehow substitute the auditory function from the outer ear to the inner ear.

In addition, promontory stimulation test (PST) also a useful tool to estimate the effectiveness of cochlear implant surgery. This test is very useful for patients with poor auditory nerve function and also for people with long-term hearing loss and also provide a way to find a correlation between the dynamic range of the auditory The PST is used as a functional tool to predict the effectiveness of cochlear implant operation and an electrical current up to 1 mA is applied to the patient as sine and pulse waveforms at different currents and frequencies. The patient's response is used as an index in auditory evaluations.

The selection of appropriate candidates for cochlear implantation is significantly important to save expenses and reduce error rate. Different tests and scans are performed before the cochlear implant surgery include examination of external, middle, and inner ear for signs of infection or abnormality, an audiogram, a trail of hearing aid use to assess its potential benefit, examining to evaluate middle and inner ear structures by taking computerized tomography (CT) scan and MRI (magnetic resonance imaging) scan, and psychological examination to observe the patient if he/she could cope with the implant. However, the cochlear implantation still fails in some cases even the tests and scans are performed successfully so far. Further, the cochlear implantation fails in some cases despite the anatomic health of the auditory pathway from the outer part to the cerebral cortex.

Currently, various devices (portable and non-portable) have been developed in this regard so far. From among these devices, a Tinitop device is used for applying electrical and acoustic stimulations simultaneously. This device uses electrical and acoustic signals with a frequency of 144 HZ. The pulse time is about 9.9 seconds and the pulse interval is about 2 seconds.

However, the available prior art do not provide an effective system and method for auditory evaluations that creates various waveforms in the range of 20 Hz to 20 kHz with different (two) isolated channels and that measures the impedance rate between the electrodes in different channels.

Henceforth, there is a need for an electrical transtympanic stimulator for examining auditory pathway from the nerve to the cortex by creating electrical sensors through auditory sensation and the electrical stimulation is applied through electrodes located in the ear canal and on the skull.

SUMMARY OF THE INVENTION

The present invention discloses a device for an auditory processing evaluation, and more particularly relates to an electrical transtympanic stimulator for auditory processing evaluation and examining the auditory pathway from the nerve to the cortex by applying electrical stimulation via electrodes that are located in the ear canal and on the skull of a patient.

In one embodiment, the electrical transtympanic stimulator is configured to examine the efficacy of cochlear implantation while assessing the patient's condition and severity of hearing loss by examining the auditory pathway using one or more electrodes to apply electrical stimulation in the ear canal. In one embodiment, the electrical transtympanic stimulator comprises a processor, a power source, an output circuit, and one or more electrodes. In one embodiment, the power source is configured to supply power to the processor and the output circuit for operating the electrical transtympanic stimulator. In an exemplary embodiment, the processor could be a field-programmable gate array (FPGA) based embedded processor. The electrodes in communication with the output circuit, configured to locate in the ear canal and on the skin around the skull of a patient, thereby performing the auditory processing evaluation by applying the current pulses to the ear canal and skull in different waveforms at various frequency ranges about 20 Hz-20 kHz with parameters such as current, voltage, and frequency.

In one embodiment, the electrical transtympanic stimulator further comprises a digital-to-analog converter, an amplifier, a voltage-to-current converter, a voltage and current measurement module, and a protection circuit. In one embodiment, the digital-to-analog converter is connected to the voltage-to-current converter via the amplifier. The amplifier is configured to amply the analogue voltage signals that are produced by the digital-to-analog converter. The electrodes are connected to the voltage-to-current converter for receiving electrical pulses i.e., current pulses/signals for applying the electrical stimulation to the patient for performing the auditory processing evaluation. In one embodiment, the voltage and current measurement module is connected to the electrodes for measuring the voltage and current values, thereby monitoring the current signals/pules applied to the patient and increasing patient's safety using the protection circuit.

In one embodiment, the digital-to-analog converter is in communication with the processor and the power source. The digital-to-analog converter is configured to convert digital signals into analogue voltage signals. In one embodiment, the voltage-to-current convertor is connected to the digital-to-analog converter via the amplifier. The voltage-to-current convertor is configured to convert the analogue voltage signals to current signals/pulses that are proportional to the analogue voltage signals.

In one embodiment, the electrodes are connected to the voltage-to-current convertor. The electrodes are configured to locate in the ear canal and on the skin around the skull of a patient, thereby performing the auditory processing evaluation by applying the current pulses to the ear canal and skull in different waveforms at various frequency ranges with the parameters via the electrodes and examining the auditory pathway by applying electrical stimulation through the electrodes located in the ear canal and on the patient's skull.

In one embodiment, the analog-to-digital converter in communication with the processor is configured to convert the current and voltage sampled values received from a current sampling and a voltage sampling into a digital number representing the magnitude of the current and voltage, respectively, and transfer to the processor, thereby monitoring the current signals/pules applied to the patient and increasing patient's safety. In one embodiment, the voltage sampling is used for measuring impedance, thereby adding impedancemetry feature for evaluating auditory pathway from the nerve to the cortex by applying electrical stimulation via electrodes that are located in the ear canal and on the skull of the patient. For this purpose, the voltage at both load ends was measured. The processor controls the operation of the electrical transtympanic stimulator by providing necessary instructions based on the current and impedance values received from the current sampling and voltage sampling. In one embodiment, the electrical transtympanic stimulator further comprises a secondary protection circuit. In one embodiment, the secondary protection circuit is configured to compare the current value with a reference threshold value using an analog comparator and disconnect the power supply if the current value exceeds the references threshold value. In one embodiment, the electrical transtympanic stimulator is configured to display impedance rates between the electrodes in both channels by connecting to a computing device, thereby displaying an error message if the impedance rates are exceeded. In one embodiment, the computing device is at least any one of a smartphone, a laptop, a computer, and a tablet.

In one embodiment, the electrical transtympanic stimulator is configured to connect to the computing device for adjusting the parameters using a software application and analysing the auditory processing evaluation by applying the electrical stimulation to the patient and also storing data related to the auditory processing evaluation. In one embodiment, the electrical transtympanic stimulator is further configured to connect to the computing device via a serial port (USART), which is provided on the electrical transtympanic stimulator. In one embodiment, the operator could adjust the parameters such as current, voltage, and frequency to desired values for effectively performing the electrical stimulation for the auditory processing evaluation. In one embodiment, the physician could adjust the parameters via a display/screen of the computing device.

In one embodiment, the electrical transtympanic stimulator is further configured to operate in three modes for providing more safety to the patient. In one embodiment, at first mode of operation, the electrical transtympanic stimulator could enable the operator or physician to adjust the supply current more than 5 mA to the electrodes. If any error is occurred or the value of the current is increased beyond the threshold value then the user will be informed by an error reporting dialog. In one embodiment, at second mode of operation, the electrical transtympanic stimulator continuously monitors the applied current to the patient and zeroing of the stimulation output if the current is increased to more than 5 mA. In one embodiment, at third mode of operation, the electrical transtympanic stimulator continuously monitors the applied current to the patient and disconnects the power supply of operational amplifiers (op-amps).

In one embodiment, the current sampling and voltage sampling are added to the electrical transtympanic stimulator. The current sampling is used for sampling the current at 10Ω resistor that is connected in series with the load and also the voltage is measured across the 10Ω resistor. In one embodiment, the voltage sampling is used for measuring impedance, thereby adding impedancemetry feature for evaluating auditory pathway from the nerve to the cortex by applying electrical stimulation via the electrodes that are located in the ear canal and on the skull of the patient. For this purpose, the voltage at both load ends was measured.

One aspect of the present disclosure is directed to an electrical transtympanic stimulator for an auditory processing evaluation, comprising: a processor; a digital-to-analog converter in communication with the processor and power source, configured to convert digital signals into analogue voltage signals; a voltage-to-current convertor in communication with the digital-to-analog converter via an amplifier, wherein the voltage-to-current convertor is configured to convert the analogue voltage signals to current signals/pulses that are proportional to the analogue voltage signals; one or more electrodes in communication with the voltage-to-current convertor, configured to locate in the ear canal and on the skin around the skull of a patient, thereby performing the auditory processing evaluation by applying the current pulses to the ear canal and skull in different waveforms at various frequency ranges with parameters via the electrodes and examining the auditory pathway by applying electrical stimulation through the electrodes located in the ear canal and on the skull; and a protection circuit configured to disconnect the power supply to the electrodes if the current value exceeds a threshold value.

In one embodiment, the electrical transtympanic stimulator is configured to connect to a computing device for adjusting the parameters using a software application and analysing the auditory processing evaluation by applying the electrical stimulation to the patient and also storing data related to the auditory processing evaluation. In another embodiment, the parameters include current, voltage, and frequency. In one embodiment, the computing device is at least any one of a smartphone, a laptop, a computer, and a tablet. In another embodiment, the electrical transtympanic stimulator has a frequency range of about 20 Hz to 20 kHz.

In one embodiment the electrical transtympanic stimulator further comprises an analog-to-digital converter, wherein the analog-to-digital converter in communication with the processor is configured to convert the current and voltage sampled values received from a current sampling and a voltage sampling into a digital number representing the magnitude of the current and voltage, respectively, thereby monitoring the current signals/pules applied to the patient and increasing patient's safety. In another embodiment, the electrical transtympanic stimulator further comprises a secondary protection circuit, configured to compare the current value with a reference threshold value using an analog comparator and disconnect the power supply if the current value exceeds the references threshold value.

In one embodiment, the electrical transtympanic stimulator is configured to display impedance rates between the electrodes in both channels by connecting to the computing device, thereby displaying an error message if the impedance rates are exceeded. In one embodiment, the amplifier is configured to amply the analogue voltage signals that are produced by the digital-to-analog converter. In another embodiment, the electrical transtympanic stimulator further comprises one or more isolated channels for producing independent stimulation in each channel. In one embodiment, the processor is a field-programmable gate array (FPGA) based embedded processor. In another embodiment, the electrical transtympanic stimulator is further configured to examine the efficacy of cochlear implantation while assessing the patient's condition and severity of hearing loss by examining the auditory pathway using the electrodes to apply electrical stimulation in the ear canal.

Another aspect of the present disclosure is directed to an electrical transtympanic stimulator for an auditory processing evaluation, comprising: a processor; a digital-to-analog converter in communication with the processor and power source, configured to convert digital signals into analogue voltage signals; a voltage-to-current convertor in communication with the digital-to-analog converter via an amplifier, wherein the voltage-to-current convertor is configured to convert the analogue voltage signals to current signals/pulses that are proportional to the analogue voltage signals; one or more electrodes in communication with the voltage-to-current convertor, configured to locate in the ear canal and on the skin around the skull of a patient, thereby performing the auditory processing evaluation by applying the current pulses to the ear canal and skull of the patient in different waveforms at various frequency ranges with parameters via the electrodes and examining the auditory pathway by applying electrical stimulation through the electrodes located in the ear canal and on the skull; a computing device connected to the electrical transtympanic stimulator for adjusting the parameters using a software application and analysing the auditory processing evaluation, wherein the parameters include current, voltage, and frequency; and a protection circuit configured to disconnect the power supply to the electrodes if the current value exceeds a threshold value. In one embodiment, the electrical transtympanic stimulator further comprises one or more isolated channels for producing independent stimulation in each channel.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The present invention generally relates to a device for an auditory processing evaluation, and more particularly relates to an electrical transtympanic stimulator for auditory processing evaluation and examining the auditory pathway from the nerve to the cortex by applying electrical stimulation via electrodes that are located in the ear canal and on the skull of a patient.

A description of embodiments of the present invention will now be given with reference to the figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
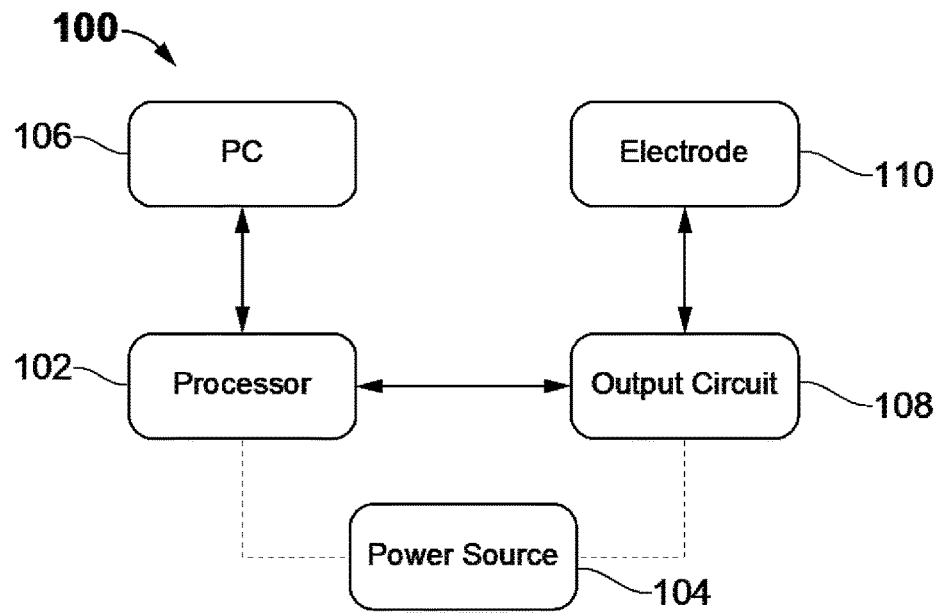
FIG. 1 illustrates a block diagram of an electrical transtympanic stimulator or tester, according to one embodiment.

Referring to FIG. 1, a block diagram of an electrical transtympanic stimulator/tester 100 in one embodiment is disclosed. In one embodiment, the electrical transtympanic stimulator 100 is configured to examine the efficacy of cochlear implantation while assessing the patient's condition and severity of hearing loss by examining the auditory pathway using one or more electrodes 110 to apply electrical stimulation in the ear canal. In one embodiment, the electrical transtympanic stimulator 100 comprises a processor 102, a power source 104, an output circuit 108, and one or more electrodes 110. In one embodiment, the power source 104 is configured to supply power to the processor 102 and the output circuit 108 for operating the electrical transtympanic stimulator 100.

In an exemplary embodiment, the processor 102 could be a field-programmable gate array (FPGA) based embedded processor. The electrodes 110 in communication with the output circuit 108, configured to locate in the ear canal and on the skin around the skull of a patient, thereby performing the auditory processing evaluation by applying the current pulses to the ear canal and skull in different waveforms at various frequency ranges about, but not limited to, 20 Hz to 20 kHz with the parameters such as current, voltage, and frequency. In one embodiment, the electrical transtympanic stimulator 100 is further configured to examine the efficacy of cochlear implantation while assessing the patient's condition and severity of hearing loss by examining the auditory pathway using the electrodes to apply electrical stimulation in the ear canal.

Figure 2:
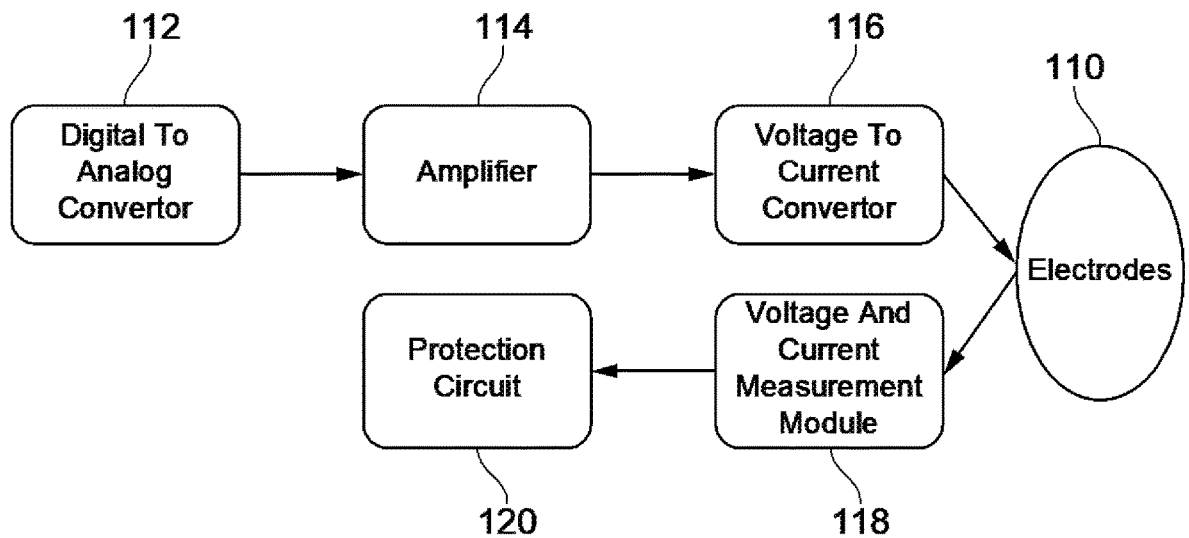
FIG. 2 illustrates a block diagram of components of the electrical transtympanic stimulator comprising a digital-to-analog converter and a voltage-to-current converter, according to one embodiment.

Referring to FIG. 2, a block diagram of the electrical transtympanic stimulator 100 comprising a digital-to-analog converter 112 and a voltage-to-current converter 116 is disclosed. In one embodiment, the electrical transtympanic stimulator 100 further comprises a digital-to-analog converter 112, an amplifier 114, a voltage-to-current converter 116, a voltage and current measurement module 118, and a protection circuit 120. In one embodiment, the digital-to-analog converter 112 is connected to the voltage-to-current converter 116 via the amplifier 114. The electrodes 110 are connected to the voltage-to-current converter 116 for receiving electrical pulses i.e., current pulses/signals for applying the electrical stimulation to the patient for performing the auditory processing evaluation. In one embodiment, the voltage and current measurement module 118 is connected to the electrodes 110 for measuring the voltage and current values, thereby monitoring the current signals/pules applied to the patient and increasing patient's safety using the protection circuit 120.

Figure 3:
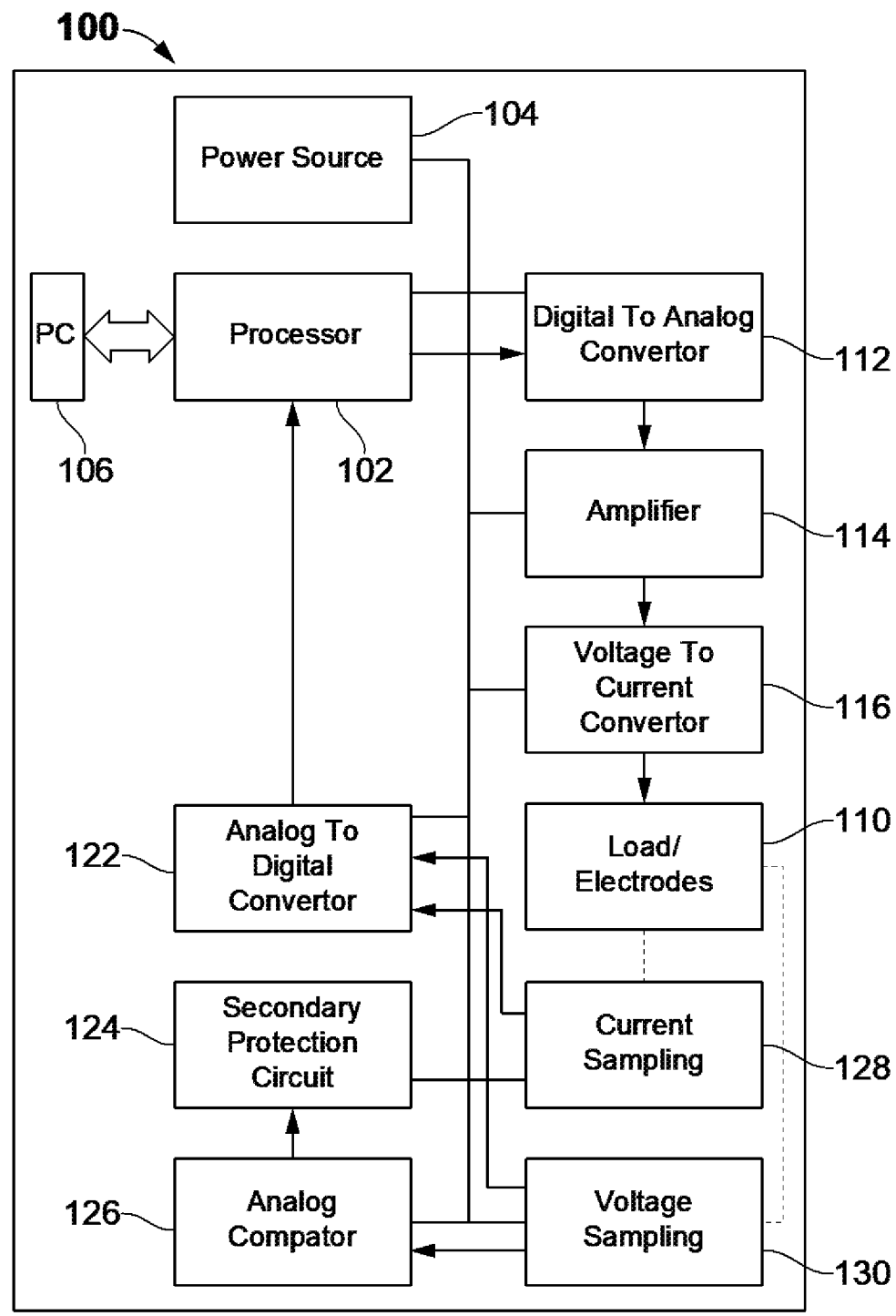
FIG. 3 illustrates a block diagram of components of the electrical transtympanic stimulator, according to one embodiment.

Referring to FIG. 3, a block diagram of components of the electrical transtympanic stimulator 100 in one embodiment is disclosed. In one embodiment, the electrical transtympanic stimulator 100 comprises a digital-to-analog converter 112, an amplifier 114, a voltage-to-current converter 116, and an analog-to-digital converter 122. In one embodiment, the digital-to-analog converter 112 is in communication with the processor 102 and the power source 104. The digital-to-analog converter 112 is configured to convert digital signals into analogue voltage signals. In one embodiment, the voltage-to-current convertor 116 is connected to the digital-to-analog converter 112 via the amplifier 114. The voltage-to-current convertor 116 is configured to convert the analogue voltage signals to current signals/pulses that are proportional to the analogue voltage signals.

In one embodiment, the electrodes 110 are connected to the voltage-to-current convertor 116. The electrodes 110 are configured to locate in the ear canal and on the skin around the skull of a patient, thereby performing the auditory processing evaluation by applying the current pulses to the ear canal and skull in different waveforms at various frequency ranges with the parameters via the electrodes 110 and examining the auditory pathway by applying electrical stimulation through the electrodes 110 located in the ear canal and on the patient's skull.

In one embodiment, the analog-to-digital converter (ADC) 122 in communication with the processor 102 is configured to convert the current and voltage sampled values received from a current sampling 128 and a voltage sampling 130 into a digital number representing the magnitude of the current and voltage, respectively, and transfer to the processor 102, thereby monitoring the current signals/pules applied to the patient and increasing patient's safety. In one embodiment, the voltage sampling 130 is used for measuring impedance, thereby adding impedancemetry feature for evaluating auditory pathway from the nerve to the cortex by applying electrical stimulation via electrodes 110 that are located in the ear canal and on the skull of the patient. For this purpose, the voltage at both load ends was measured.

The processor 102 controls the operation of the electrical transtympanic stimulator 100 by providing necessary instructions based on the current and impedance values received from the current sampling 128 and voltage sampling 130. In one embodiment, the electrical transtympanic stimulator 100 further comprises a secondary protection circuit 124. In one embodiment, the secondary protection circuit 124 is configured to compare the current value with a reference threshold value using an analog comparator 126 and disconnect the power supply if the current value exceeds the references threshold value. In one embodiment, the electrical transtympanic stimulator 100 is configured to display impedance rates between the electrodes in both channels by connecting to a computing device 106, thereby displaying an error message if the impedance rates are exceeded. In one embodiment, the electrical transtympanic stimulator 100 further comprises a reset generator, clocks, SER_IN, SER_OUT, a DAC controller, and an ADC controller.

In one embodiment, the electrical transtympanic stimulator 100 could be used for performing transtympanic promontory stimulation test (TPST), diagnosing and treating of tinnitus, usability in recording the electrical auditory brainstem responses (EABR), and used for rehabilitation of balance system.

Figure 4:
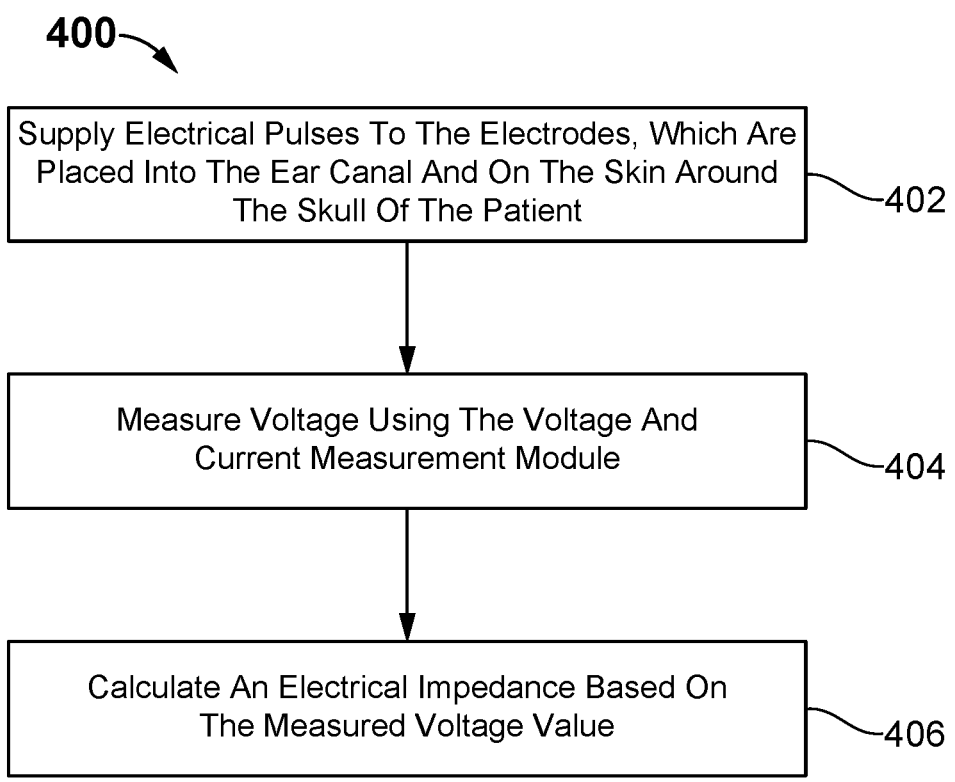
FIG. 4 illustrates a flowchart of a method for measuring an electrical impedance between the electrodes, according to one embodiment.

Referring to FIG. 4, a flowchart of a method 400 for measuring an electrical impedance between the electrodes 110 in one embodiment is disclosed. In one embodiment, the method 400 comprising the steps of: at step 402, the electrical pulses are supplied to electrodes 110, which are placed into the ear canal and on the skin around the skull of the patient. At step 404, the voltage is measured using the voltage and current measurement module 118 (shown in FIG. 2). Further, at step 406, the electrical impedance is calculated based on the measured voltage.

Figure 5:
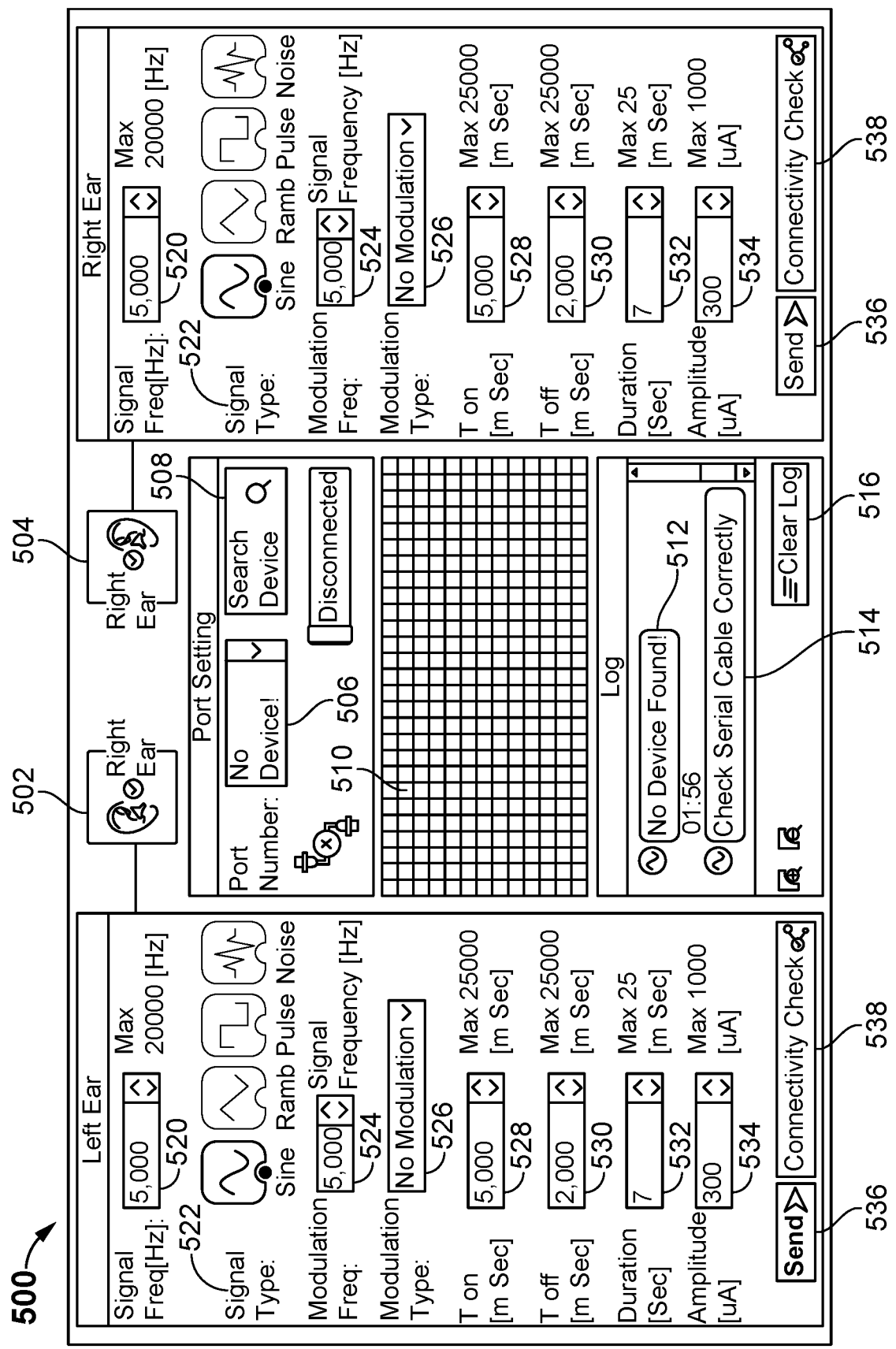
FIG. 5 illustrates a screenshot of the electrical stimulation for an auditory processing evaluation using the computing device, according to one embodiment.

Referring to FIG. 5, a screenshot 500 of a user interface of the computing device for an auditory processing evaluation using the computing device 106 in one embodiment is disclosed. In one embodiment, the electrical transtympanic stimulator 100 is further configured to connect to the computing device 106 via a serial port (USART). In one embodiment, the computing device 106 is at least any one of a smartphone, a laptop, a computer, and a tablet. In one embodiment, the electrical transtympanic stimulator 100 is configured to connect to the computing device 106 for adjusting the parameters such as current, voltage, and frequency using a software application via the user interface and analysing the auditory processing evaluation by applying the electrical stimulation to the patient and also storing data related to the auditory processing evaluation. In one embodiment, the software application could enable the physician to add subsequently all inputs, outputs, and system clock. In one embodiment, the information is transmitted to the processor 102, i.e. the main brain of the system, in the form of encoded strings. In this section, based on the input information, the signals are digitally generated, placed in the processor output and the stimulation output is sent. Some part of the programs written to generate the stimulation.

In one embodiment, the screenshot 500 shows multiple icons and buttons for adjusting parameters include, but not limited to, a signal frequency 520, signal type 522, frequency modulation 524, modulation type 526, on-time 528, off-time 530, time duration 532, and amplitude 534, send 536, and connectivity check 538, etc. on either side of a left ear 502 and right ear 504. In one embodiment, the operator could adjust the parameters such as current, voltage, and frequency to desired values for effectively performing the electrical stimulation for the auditory processing evaluation.

In one embodiment, the screenshot 500 shows a display/screen 510 for displaying signals in different waveforms such as sine wave, ramp wave, pulse, and noise at various frequency ranges. In one embodiment, the screenshot 500 shows icons include, but not limited to, a port number 506, a search device 508, error notifications, for example, no device found 512 and check serial cable connect correctly 514. In one embodiment, the operator could clear the log using a clear log 516. The computing device 106 receives all the commands desired by the user via the user interface as encoded frames and performs the operation intended by the user. The user interface is actually the software that is installed on the computing device and provides a space in front of the user that enables the user to conduct the auditory evaluation process to easily perform and direct a successful electrical stimulation using the software menus. In the software, it is possible to change the waveform, frequency, amplitude and signal activation/non-activation time.

Figure 6:
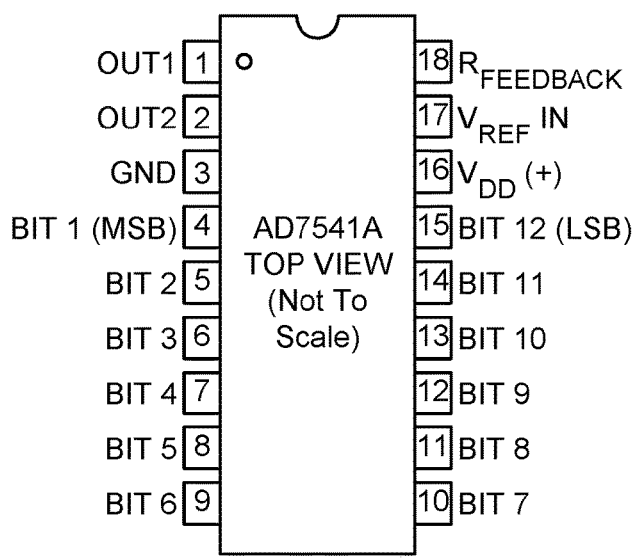
FIG. 6 illustrates a digital-to-analog converter (DAC) of the electrical transtympanic stimulator, according to one embodiment.
Figure 7:
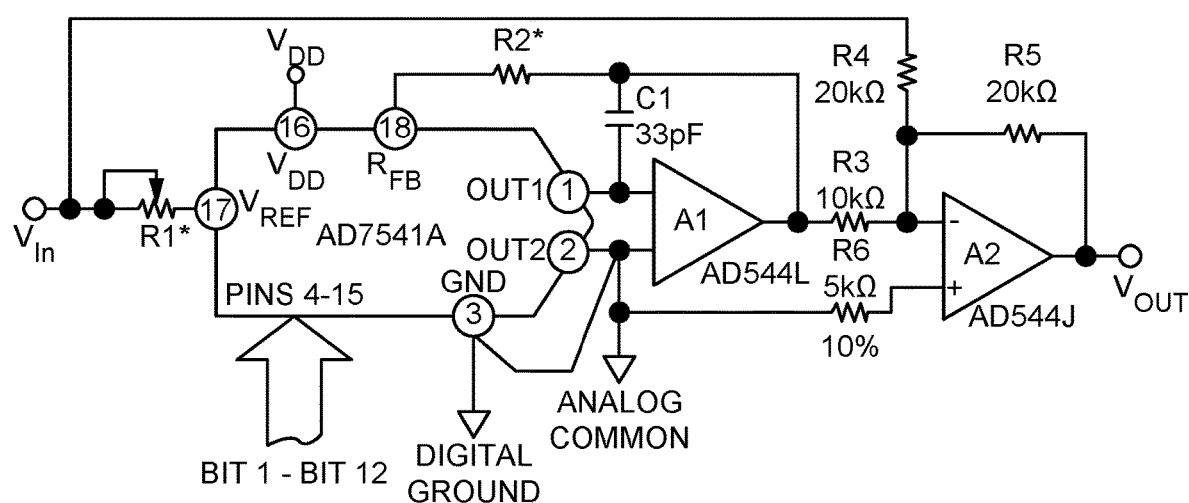
FIG. 7 illustrates a circuit diagram of an amplifier used in the electrical transtympanic stimulator, according to one embodiment.

Referring to FIG. 6, the digital-to-analog converter (DAC) 112 of the electrical transtympanic stimulator in one embodiment is disclosed. In one embodiment, the digital-to-analog converter 112 is a 12-bit DAC for achieving high resolution and increased voltage levels (step reduction). Referring to FIG. 7, a circuit diagram of the amplifier 114 used in the electrical transtympanic stimulator 100 in one embodiment is disclosed. In one embodiment, the amplifier 114 is placed between the digital-to-analog converter 112 and the voltage-to-current converter 116. The amplifier 114 is configured to amply the analogue voltage signals that are produced by the digital-to-analog converter 112. In an exemplary embodiment, an operational amplifier with high Slew Rate, low input offset and high bandwidth is used.

Figure 8:
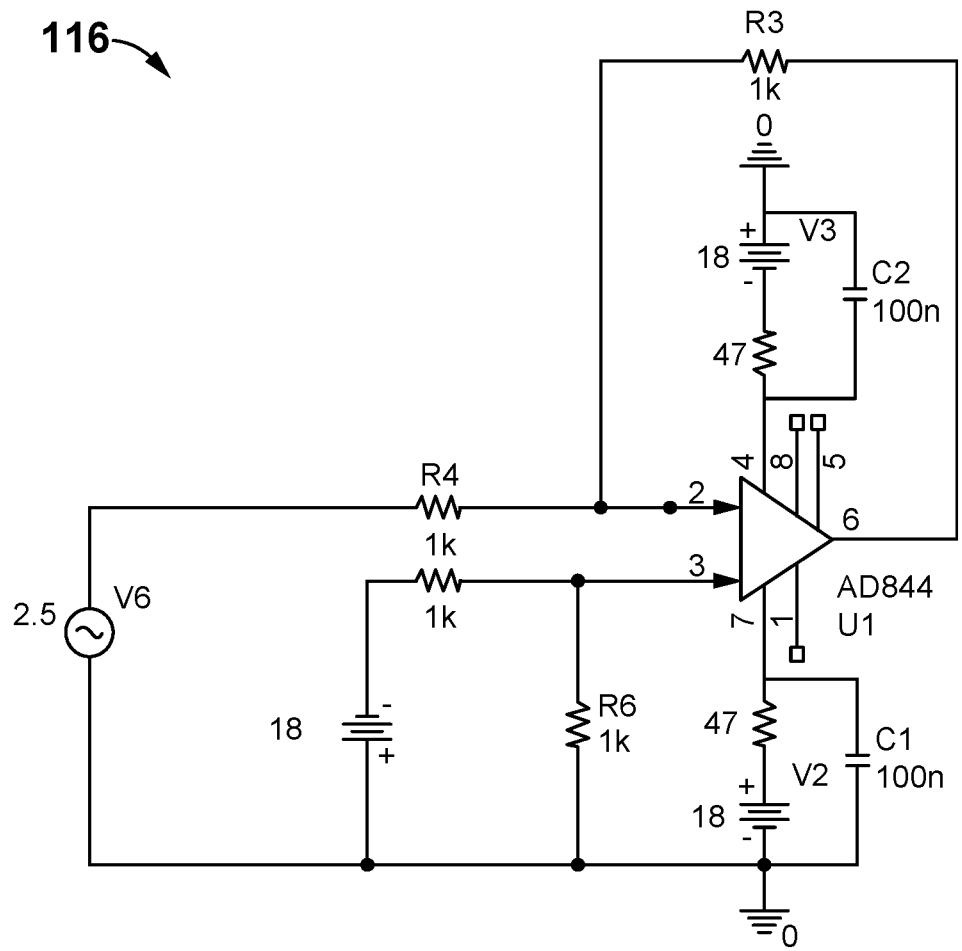
FIG. 8 illustrates a voltage-to-current converter used in the electrical transtympanic stimulator, according to one embodiment.

Referring to FIG. 8, the voltage-to-current converter 116 used in the electrical transtympanic stimulator 100 in one embodiment is disclosed. In one embodiment, the voltage-to-current converter 116 is configured to convert the analogue voltage signals to current signals/pulses that are proportional to the analogue voltage signals. The voltage-to-current converter 116 provides accurate response to test independency of current source from the load resistor, linearity of input voltage and output current at a constant load $R_L$, output current linearity at different frequencies and at a constant load resistor $R_{L5}$. A simple overview of the current source circuit designed using an operational amplifier is illustrated in the FIG. 8, in which the above-mentioned problems are partially resolved.

Figure 9:
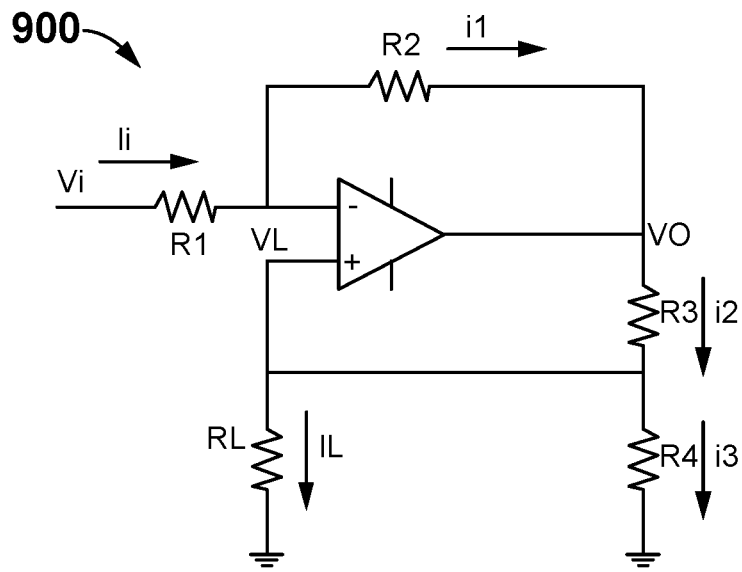
FIG. 9 illustrates a circuit diagram of a current source used in the electrical transtympanic stimulator, according to one embodiment.

Referring to FIG. 9, a circuit diagram of a current source 900 used in the electrical transtympanic stimulator 100 in one embodiment is disclosed. In one embodiment, the voltage and current relation obtained from the current source circuit 900 is as follows:

$$\left.\begin{array}{l} i_i = \dfrac{V_i - V_L}{R_1} \\ i_1 = \dfrac{V_L - V_0}{R_2} \end{array}\right\} \Rightarrow V_0 = V_L - \dfrac{R_2}{R_1}(V_i - V_L) \qquad (I)$$

$$i_L = i_2 - i_3 \Rightarrow i_L = V_L - \dfrac{R_2}{R_1 R_3}(V_i - V_L) - V_L - \dfrac{V_L}{R_4} \Rightarrow i_L =$$

$$\dfrac{-R_2}{R_1 R_3}V_i + \dfrac{R_2}{R_1 R_3}V_L - \dfrac{V_L}{R_4} = -\dfrac{R_2}{R_1 R_3}V_i + \left(\dfrac{R_2}{R_1 R_3} - \dfrac{1}{R_4}\right)V_L$$

$$\dfrac{R_2}{R_1 R_3} - \dfrac{1}{R_4} = 0 \Rightarrow R_1 R_3 = R_2 R_4 \Rightarrow i_L = \dfrac{-R_2}{R_1 R_3}V_i$$

In one embodiment, the output current is independent of the load voltage $V_L$, that is, by changing the load resistor $R_L$ and consequently the output voltage $V_O$, the output current does not change, but here that the $i_L$ becomes a coefficient of $V_{L1}$, so for this purpose the $V_{L1}$ coefficient assumes as zero to eliminate the dependency.

In order for the output voltage to be independent of the load voltage, relation (I) must be established and according to this equation, we must select the resistors in such a way that this relation could be most likely met; and also to select the resistors, other issues should be taken into account, such as the saturation of the op amp.

To prevent op amp from going towards current saturation, the selected resistor $R_3$ should be as small as possible. And in the above-mentioned relation, the resistor $R_3$ is inversely related to the $i_L$ current, so the smaller the resistor is selected, the higher the current $i_L$ is obtained. The resistor $R_3$ is so selected as to limit the current $i_L$ flowing in the current source circuit 900.

Figures 10, 11:
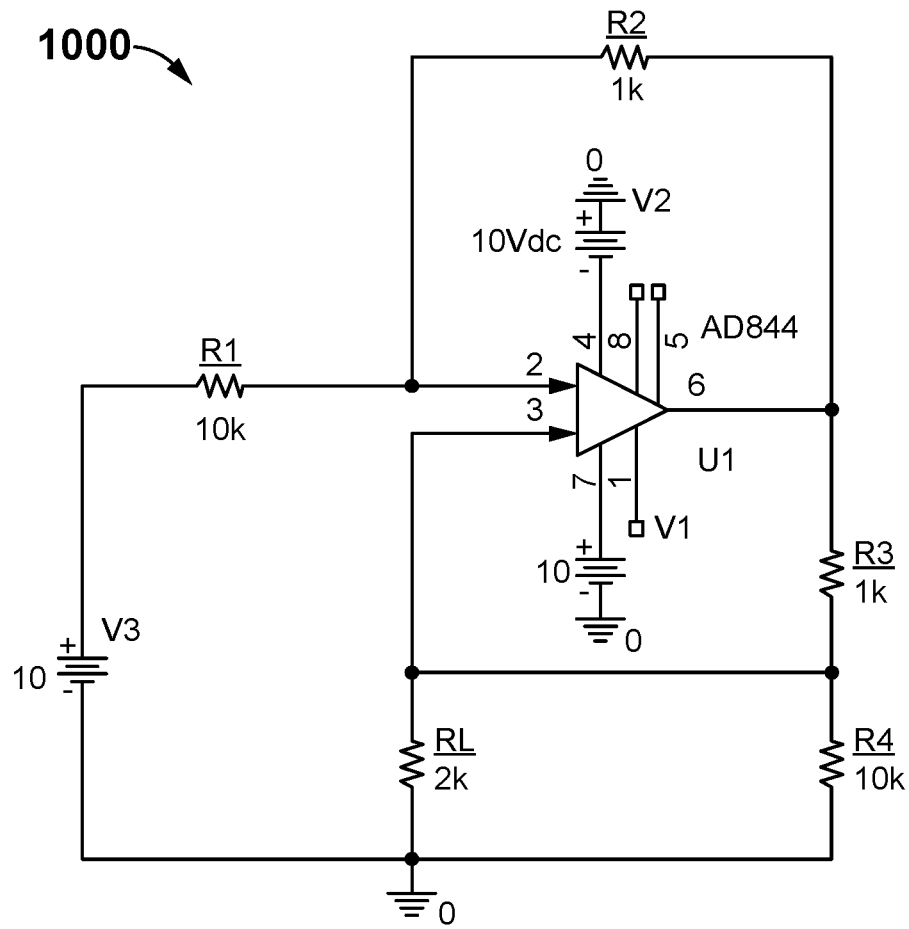
FIG. 10 illustrates a simulated voltage-to-current converter circuit, according to one embodiment.
FIG. 11 illustrates a table shows the obtained current values i.e., load current $I_L$ from the circuit of the current source by conducting simulation and practical tests, according to one embodiment.

Referring to FIG. 10, a simulated voltage-to-current converter circuit 1000 in one embodiment is disclosed. In one embodiment, the simulated voltage-to-current converter circuit 1000 used to test and measure the independency of the load current $I_L$ from the load resistor $R_L$ at a constant input voltage and also could change the load resistor $R_L$ to observe if the load current $I_L$ remains constant or not.

Referring to FIG. 11, a table 1100 shows obtained current values i.e., load current $I_L$ from the circuit of the current source 900 by conducting simulation and practical tests is disclosed. In one embodiment, the load current $I_L$ is measured from the current source circuit 900 by conducting simulation and practical tests. The load current $I_L$ is measured on independency of the load resistor $R_L$ at a constant input voltage. In one embodiment, the load current $I_L$ is measured about 500 µA and 490 µA by conducting the simulation and practical tests, respectively, at different load resistances $R_L$ of 1K, 2K, 5.6K, and 8.6K ohms and at a constant input voltage. In one embodiment, the load current $I_L$ is measured about 500 µA and 482 µA by conducting the simulation and practical tests, respectively, at the load resistance $R_L$ of 10K ohms. In one embodiment, the current $I_L$ is measured about 491 µA and 481 µA by conducting the simulation and practical tests, respectively, at the load resistance $R_L$ of 12K ohms.

Figures 12, 13:
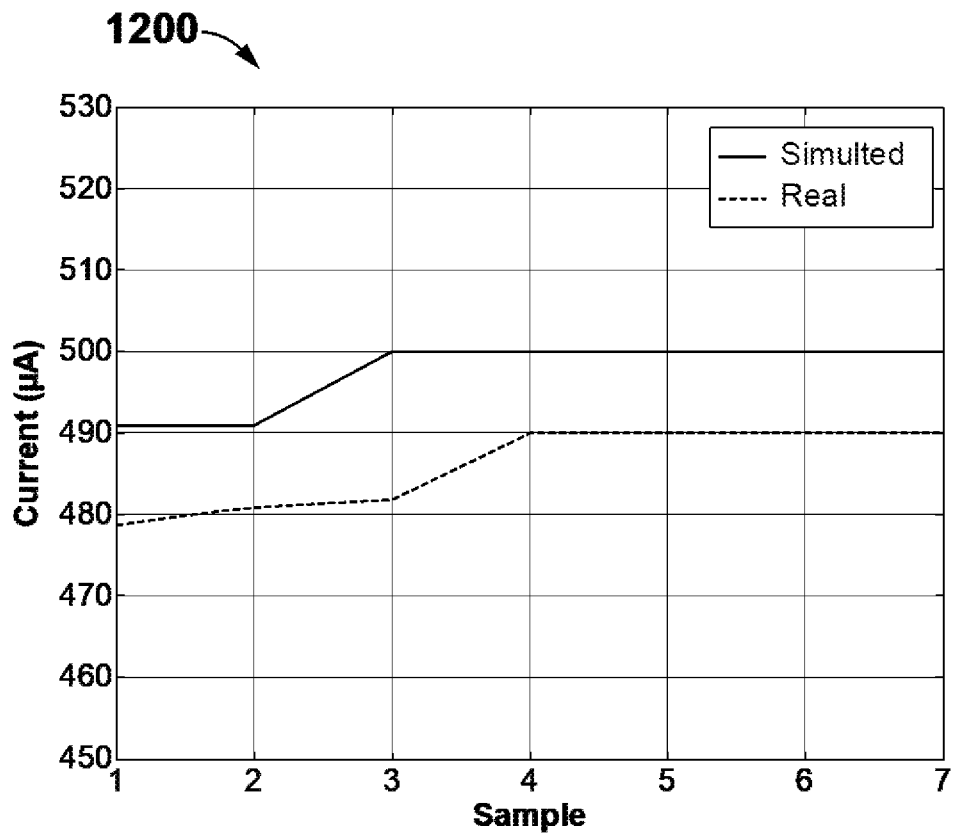
FIG. 12 illustrates a graph shows the results of simulation and practical tests, according to one embodiment.
FIG. 13 illustrates a table shows the test result of the input voltage $V_i$ and load current $I_L$ at constant load resistance $R_L$, according to one embodiment.

Referring to FIG. 12, a graph 1200 shows the results of simulation and practical tests are disclosed. In one embodiment, the graph 1200 shows the current curves (1202 and 1204), which are generated by conducting simulation and practical tests, respectively. The current curves (1202 and 1204) represents variation in load currents $I_L$ (µA) with respective to the load resistances $R_L$ (KΩ). The current values are linearly increased at 2K ohms and 3K ohms in simulation and practical tests, respectively and the current values are further constant at 3K ohms and 4K ohms in simulation and practical tests, respectively.

Referring to FIG. 13, a table 1300 shows the test result of the input voltage $V_i$ and load current $I_L$ at constant load resistance $R_L$ is disclosed. In one embodiment, the load current $I_L$ is linearly increased by increasing input voltage $V_i$. The load current $I_L$ is varied from about 1 µA to 450 µA by changing the input voltage $V_i$ from about 0 to 5V. In one embodiment, the load resistance $R_L$ is fixed at 10.67 KΩ.

Figure 14:
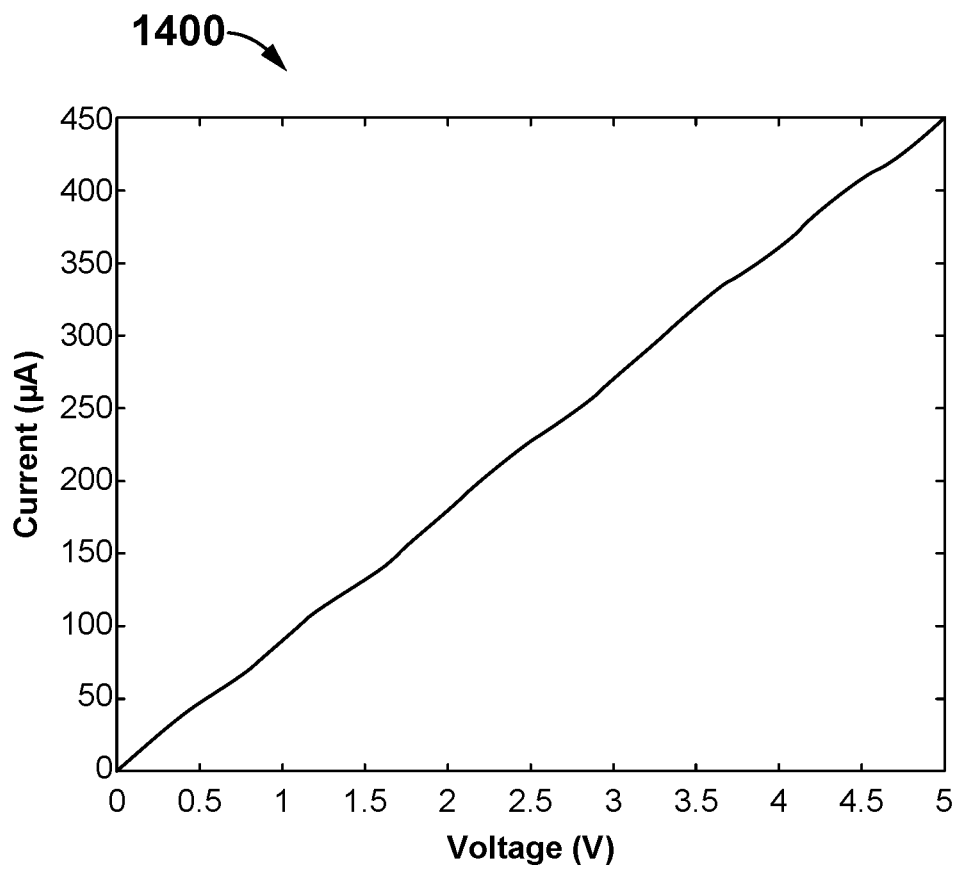
FIG. 14 illustrates a graph shows the test result of the input voltage $V_i$ and load current $I_L$ at constant load resistance $R_L$, according to one embodiment.

Referring to FIG. 14, a graph 1400 shows the test result of the input voltage $V_i$ and load current $T_L$ at constant load resistance $R_L$ is disclosed. In one embodiment, the graph 1400 shows a current and voltage curve that represents variation in load currents $I_L$ (µA) with respective to the input voltage $V_i$ at a constant load resistances $R_L$ 10.67 KΩ. The linearity of the load current $I_L$ at different frequencies and at a constant load resistor $R_L$ are measured by increasing the input voltage ($V_i$) amplitude and study the variations of the load current $I_L$ at different frequencies.

Figure 15:
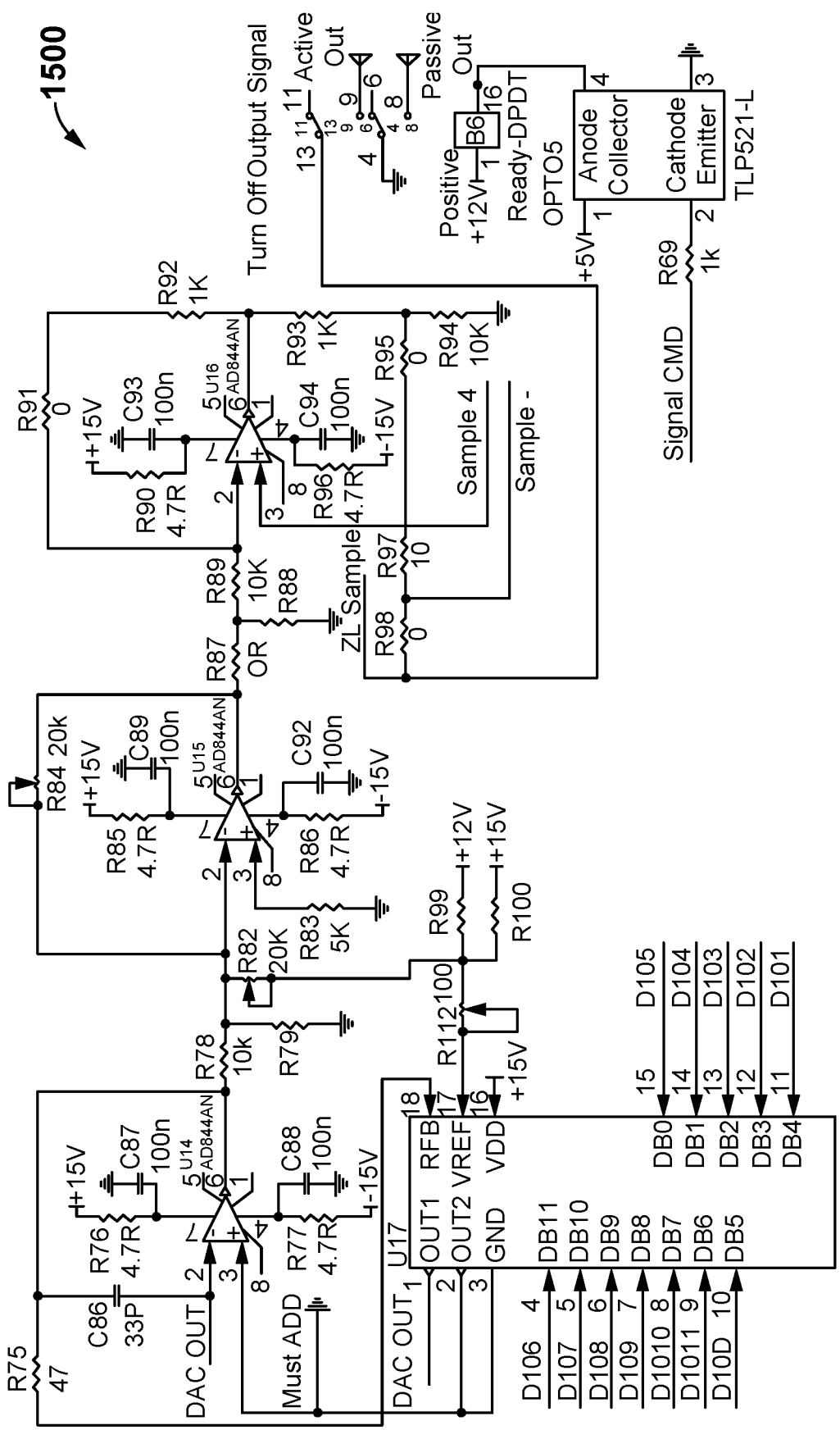
FIG. 15 illustrates a simulated circuit of the electrical transtympanic stimulator for observing output voltage variations, according to one embodiment.

Referring to FIG. 15, a simulated circuit 1500 of the electrical transtympanic stimulator for observing output voltage variations in one embodiment is disclosed. In one embodiment, the variations of the output voltage could be observed at two resistor ends in relation to the required currents at a constant resistor.

In one embodiment, the electrical transtympanic stimulator 100 is further configured to operate in three modes for providing more safety to the patient. In one embodiment, at first mode of operation, the electrical transtympanic stimulator 100 could enable the operator or physician to adjust the supply current more than 5 mA to the electrodes 110 (shown in FIG. 3). If any error is occurred or the value of the current is increased beyond the threshold value then the user will be informed by an error reporting dialog. In one embodiment, at second mode of operation, the electrical transtympanic stimulator 100 continuously monitors the applied current to the patient and zeroing of the stimulation output if the current is increased to more than 5 mA. In one embodiment, at third mode of operation, the electrical transtympanic stimulator 100 continuously monitors the applied current to the patient and disconnects the power supply of operational amplifiers (op-amps).

In one embodiment, the current sampling 128 (shown in FIG. 3) and voltage sampling 130 (shown in FIG. 3) are added to the electrical transtympanic stimulator 100. The current sampling 128 is used for sampling the current at 10Ω resistor that is connected in series with the load and also the voltage is measured across the 10Ω resistor. In one embodiment, the voltage sampling 130 is used for measuring impedance, thereby adding impedancemetry feature for evaluating auditory pathway from the nerve to the cortex by applying electrical stimulation via the electrodes 110 that are located in the ear canal and on the skull of the patient. For this purpose, the voltage at both load ends was measured.

Figure 16:
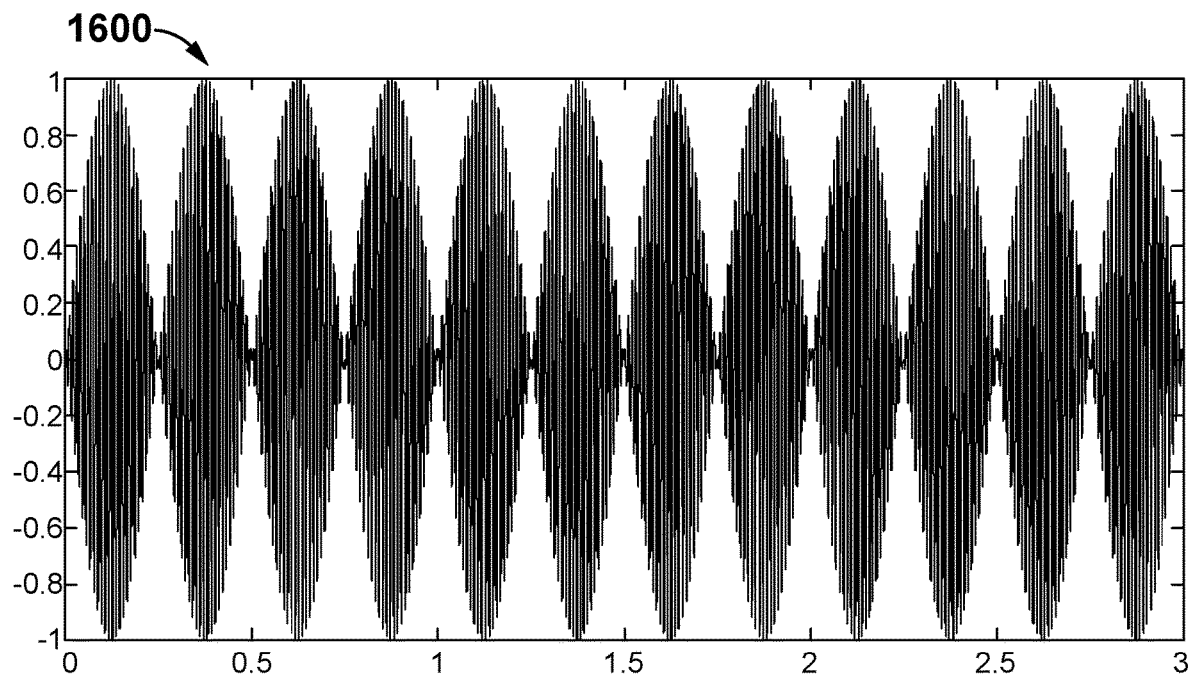
FIG. 16 illustrates a voltage-to-current converter used in the electrical transtympanic stimulator, according to one embodiment.

Referring to FIG. 16, a graph 1600 shows a current waveform in one embodiment is disclosed. In one embodiment, the electrical transtympanic stimulator 100 is configured to apply the current pulses to the ear canal and skull in different waveforms at various frequency ranges with parameters via the electrodes and examining the auditory pathway by applying the electrical stimulation. The waveforms include such as a sine wave, ramp wave, pulse, and noise at various frequency ranges. In one embodiment, the graph 1600 shows sinusoidal pulses of the current applied to the electrodes 110 for applying the electrical stimulation.

Figure 17:
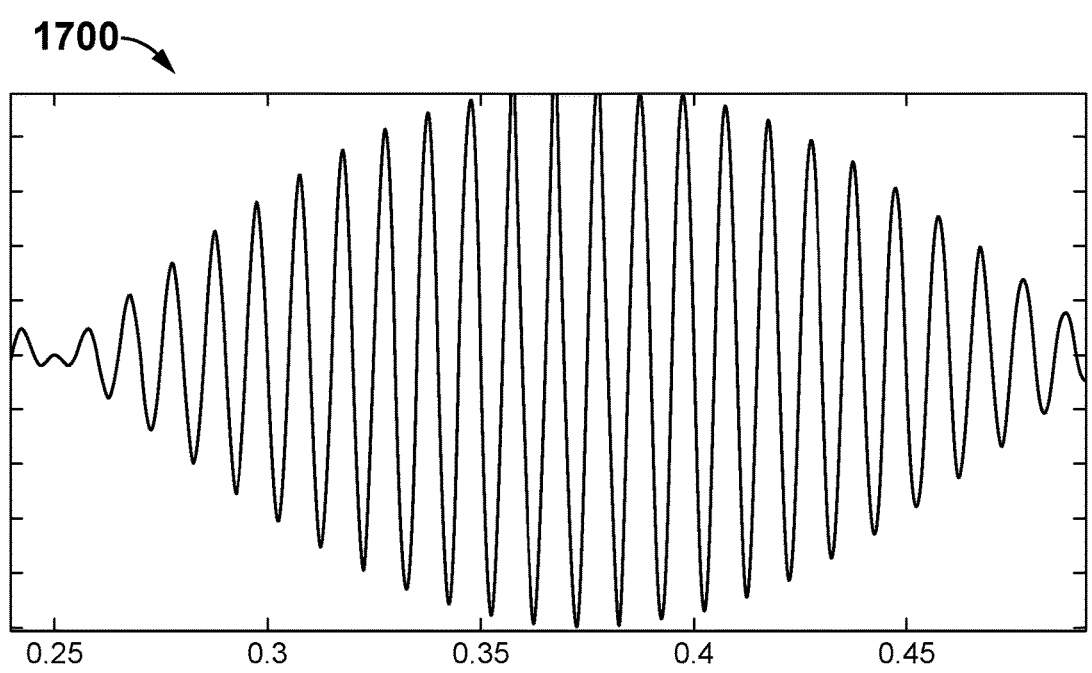
FIG. 17 illustrates a graph shows an amplitude modulation waveform of the applied current pulses, according to one embodiment.
Figure 18:
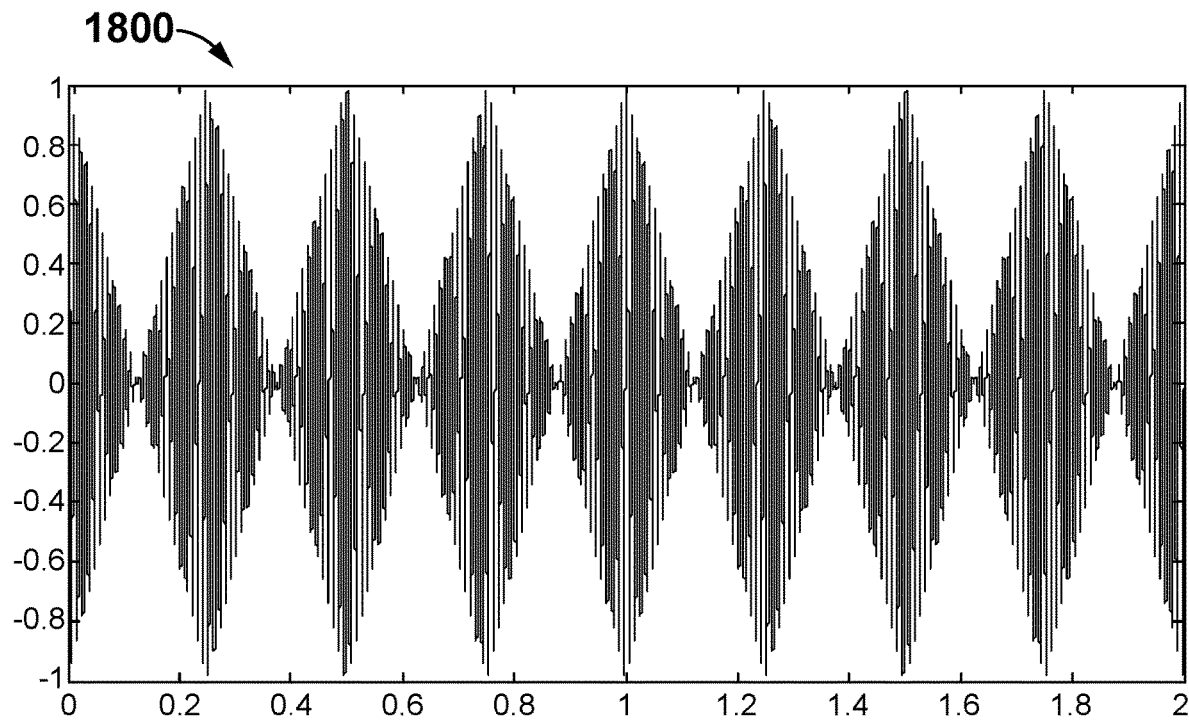
FIG. 18 illustrates a graph shows a frequency modulation waveform of the applied current pulses, according to one embodiment.

Referring to FIG. 17, a graph 1700 shows an amplitude modulation waveform of the applied current pulses in one embodiment is disclosed. In one embodiment, the current pulses are applied to the electrodes 110 in a sinusoidal waveform by changing the amplitude. Referring to FIG. 18, a graph 1800 shows a frequency modulation waveform of the applied current pulses in one embodiment is disclosed. In one embodiment, the current pulses are applied to the electrodes 110 in a sinusoidal waveform by changing the frequency.

Figure 19:
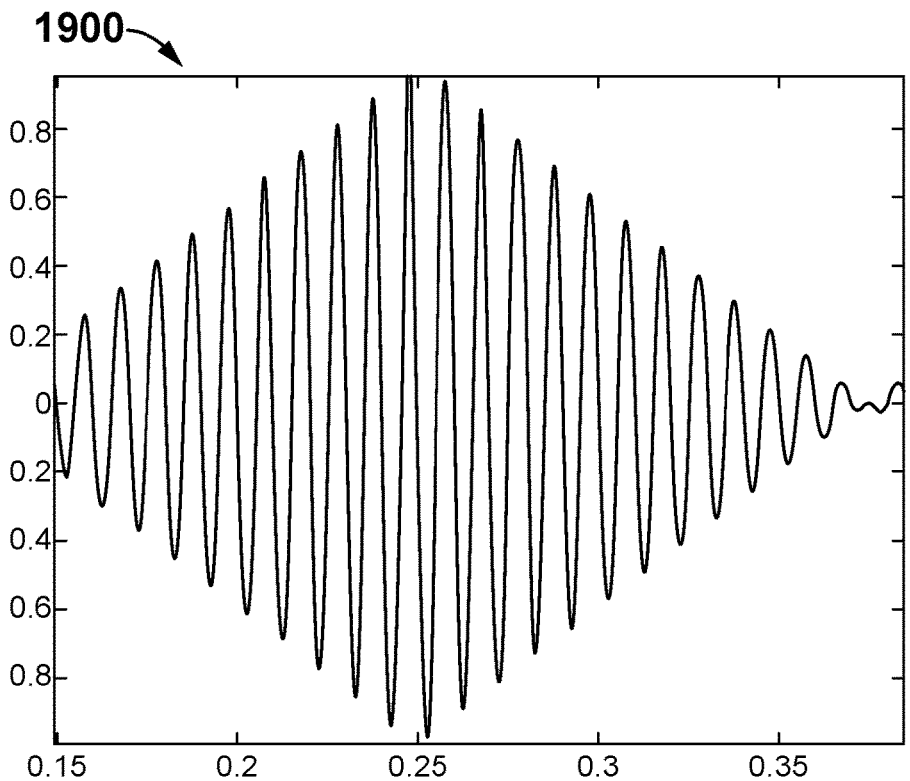
FIG. 19 illustrates a graph shows an amplitude modulation waveform of the applied current pulses, according to one embodiment.
Figure 20:
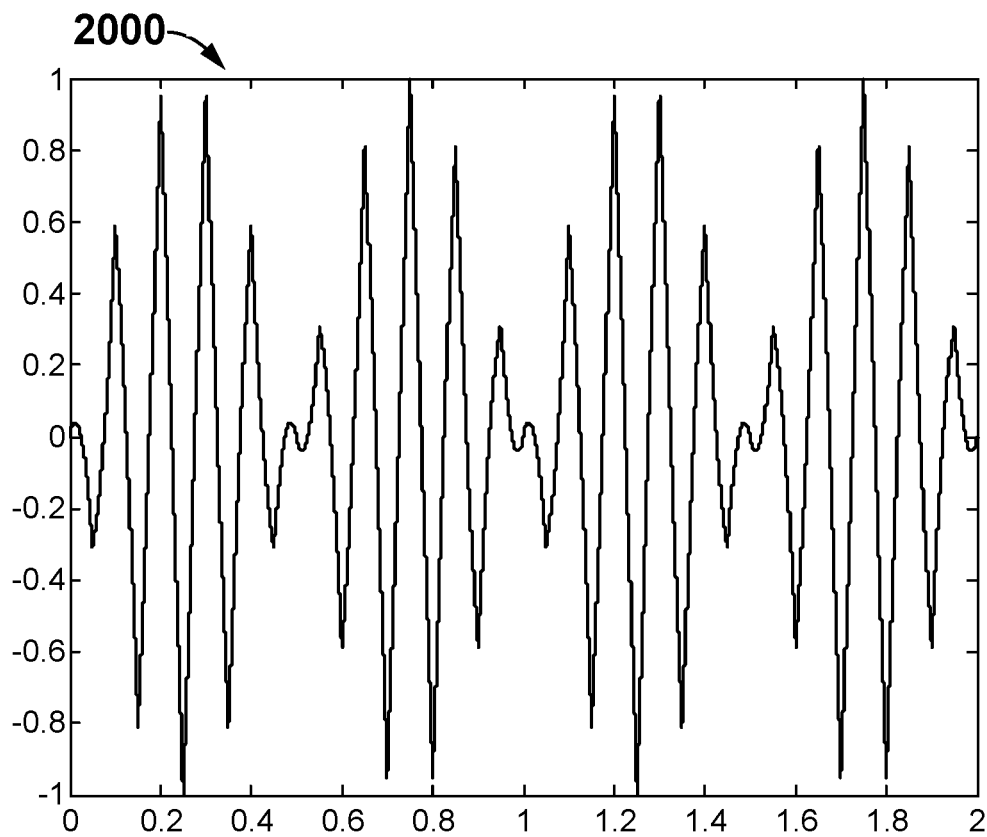
FIG. 20 illustrates a graph shows an amplitude modulation waveform of the applied current pulses, according to one embodiment.

Referring to FIG. 19, a graph 1900 shows an amplitude modulation waveform of the applied current pulses in one embodiment is disclosed. Referring to FIG. 20, a graph 2000 shows an amplitude modulation waveform of the applied current pulses in one embodiment is disclosed. In one embodiment, the physician or operator could adjust the amplitude of the current for applying the electrical stimulation to the patient.

Figure 21:
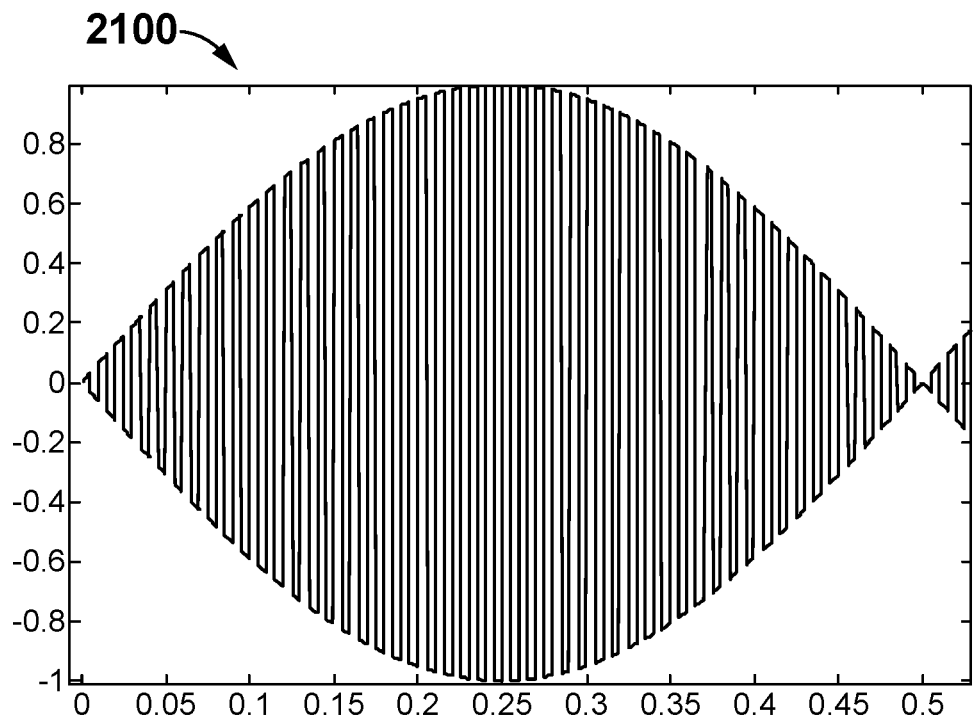
FIG. 21 illustrates a graph shows a pulse amplitude modulation waveform of the applied current, according to another embodiment.

Referring to FIG. 21, a graph 2100 shows a pulse amplitude modulation waveform of the applied current in one embodiment is disclosed. The pulse amplitude modulation is a technique in which the amplitude of each pulse is controlled by the instantaneous amplitude of the modulation signal.

Figure 22:
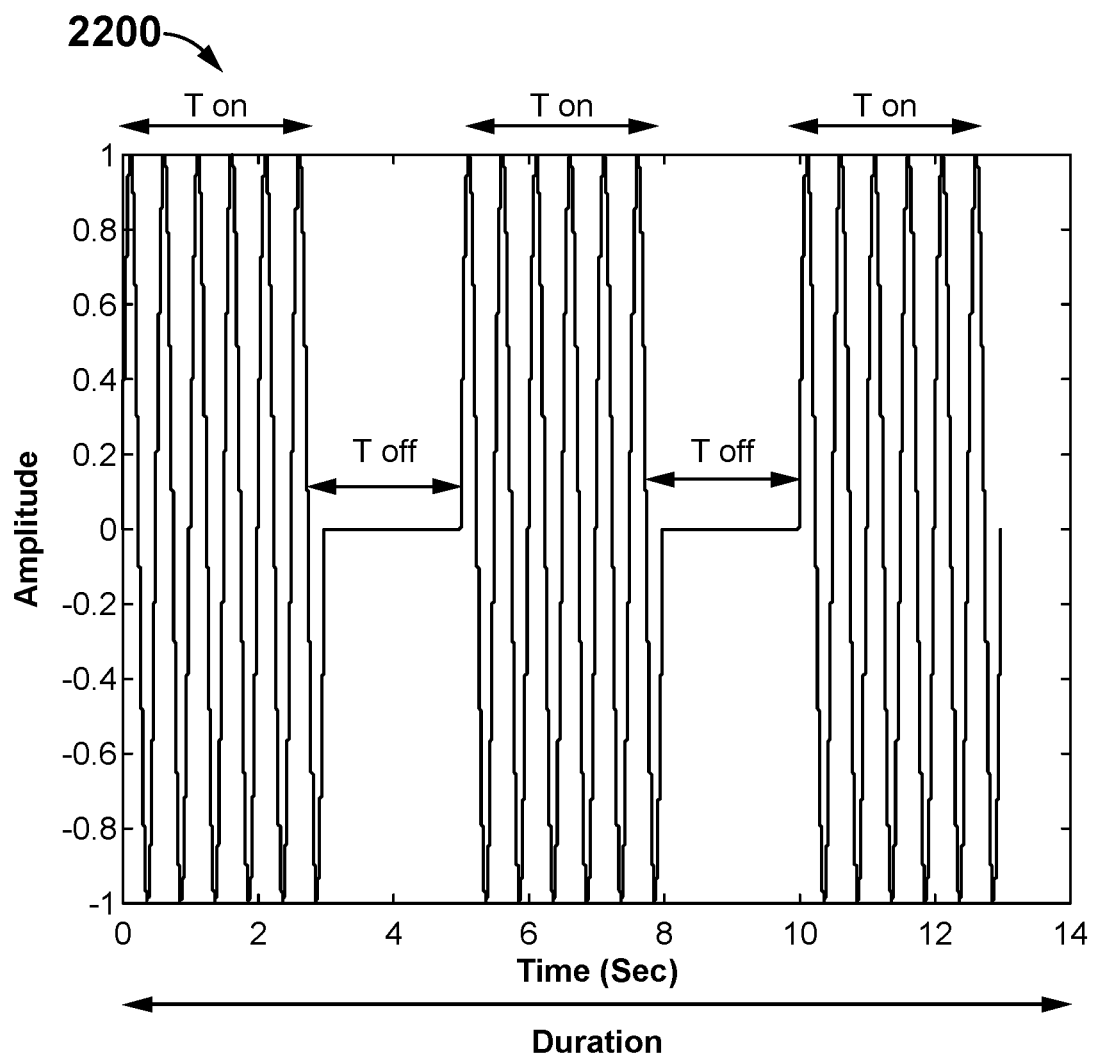
FIG. 22 illustrates a graph shows time-on and time-off of amplitude of the applied current with respect to time period, according to one embodiment.

Referring to FIG. 22, a graph 2200 shows time-on and time-off of amplitude of the applied current with respect to time period is disclosed. In one embodiment, the physician or operator could turn on and turn off of the amplitude of the current with respect to the time period for applying the electrical stimulation to the patient for examining the auditory pathway through the electrodes located in the ear canal and on the skull of the patient.

Before cochlear implantation and in order to measure the efficiency of the patient's auditory nerves the electrical transtympanic stimulator 100 is used in such a way that the electrodes 110 are inserted into the ear canal and on the forehead of the patient, and after applying stimulations at different amplitudes and frequencies, the patient's auditory feedback is measured and accordingly, suitable cases, which are most likely to have postoperative treatment, are selected for the surgery. In addition, for patients suffering from tinnitus, the electrical transtympanic stimulator 100 is able to evaluate the extent and type of tinnitus by providing varied and different stimulation patterns, and then based on the data obtained, the electrical stimulation-based therapeutic methods will be applied.

The advantages of the present invention include, the electrical transtympanic stimulator 100 has at least two isolated channels with the ability to generate two different stimulations. The electrical transtympanic stimulator 100 determines and modulates different waveforms include, but not limited to, sine, square, and triangular waveforms. The electrical transtympanic stimulator 100 could measure impedance using the voltage sampling 130, thereby adding impedancemetry feature for evaluating auditory pathway from the nerve to the cortex by applying electrical stimulation via the electrodes 110 that are located in the ear canal and on the skull of the patient.

The electrical transtympanic stimulator 100 monitors the current values, thereby proving more safety to the patient and checks the proper attachment of the electrodes 110 while stimulation. The electrical transtympanic stimulator 100 could be used for multi-purpose applications, including subjective TPST, objective TPST, tinnitus relief, balance system rehabilitation. The electrical transtympanic stimulator 100 could record and store data related to stimulation protocols.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions.

Although specific terms may be employed herein, they are used only in generic and descriptive sense and not for purposes of limitation. Accordingly, the present invention is not limited to the specific embodiments illustrated herein. While the above is a complete description of the preferred embodiments of the invention, various alternatives, modifications, and equivalents may be used. Therefore, the above description and the examples should not be taken as limiting the scope of the invention, which is defined by the appended claims.

What is claimed is:

1. An electrical transtympanic stimulator for an auditory processing evaluation, comprising:
    a processor;
    a power source;
    an amplifier;
    a computing device having a display;
    a reference threshold value;
    a digital-to-analog converter in communication with the processor and the power source, configured to convert digital signals from the processor into analogue voltage signals;
    a voltage-to-current convertor in communication with the digital-to-analog converter via the amplifier, wherein the voltage-to-current convertor is configured to convert the analogue voltage signals to current signals/pulses that are proportional to the analogue voltage signals;
    a voltage and current measurement module configured to measure voltage and current of the current signals/pulses and to measure impedance rates using the measured voltage;
    a plurality of electrodes in communication with the voltage-to-current convertor, one electrode of the plurality of electrodes configured to locate in the ear canal and another electrode of the plurality of electrodes configured to be located on the skin around the skull of a patient, performing the auditory processing evaluation by applying the current signals/pulses to the ear canal and skull wherein the processor controls the digital to analog converter
    to adjust the signals/pulses to have different waveforms at various frequency ranges and conveyed via the plurality of electrodes and examining the auditory pathway by applying the current signals/pulses through the plurality of electrodes located in the ear canal and on the skull;
    one or more isolated channels, each channel including two or more additional electrodes to apply the current signals/pulses; the electrical transtympanic stimulator is configured to display an error message when the impedance rate is exceeded between the electrodes in the one or more channels via connection to the computing device's display; and a protection circuit configured to disconnect the power supply from the plurality of electrodes when a value of the current signals/pulses exceeds the reference threshold value as measured by the voltage and current measurement module.

2. The electrical transtympanic stimulator of claim 1, wherein the processor is configured to connect to the computing device for adjusting parameters of the current signals/pulses, which includes adjusting current, voltage, and frequency and analyzing the auditory processing evaluation by applying the current signals/pulses to the patient and also storing data obtained from the computing device related to the auditory processing evaluation.

3. The electrical transtympanic stimulator of claim 2, wherein the computing device is at least any one of a smartphone, a laptop, a computer, and a tablet.

4. The electrical transtympanic stimulator of claim 2, further comprising an analog-to-digital converter, wherein the analog-to-digital converter is in communication with the processor and is configured to convert the current and voltage as measured by the voltage and current measurement module into a digital number representing the magnitude of the sampled current and voltage, respectively, thereby monitoring the current signals/pules applied to the patient and increasing patient's safety.

5. The electrical transtympanic stimulator of claim 1, wherein the frequency ranges can comprise any value within the range of 20 Hz to 20 kHz.

6. The electrical transtympanic stimulator of claim 1, further comprising an analog comparator and a secondary protection circuit,
    the analog comparator configured to compare the measure value of the current signals/pulses with the reference threshold value, wherein the secondary protection circuit disconnects the power supply when the compared value of the current signals/pulses exceeds the reference threshold value.

7. The electrical transtympanic stimulator of claim 1, wherein the amplifier is configured to amplify the analogue voltage signals that are produced by the digital-to-analog converter.

8. The electrical transtympanic stimulator of claim 1, wherein the processor contains a field-programmable gate array (FPGA) based embedded processor.

9. An electrical transtympanic stimulator for an auditory processing evaluation, comprising:
    a processor;
    a power source;
    an amplifier;
    a computing device having a display;
    a reference threshold value;
    a digital-to-analog converter in communication with the processor and the power source, configured to convert digital signals from the processor into analogue voltage signals;
    a voltage-to-current convertor in communication with the digital-to-analog converter via the amplifier, wherein the voltage-to-current convertor is configured to convert the analogue voltage signals to current signals/pulses that are proportional to the analogue voltage signals;

a voltage and current measurement module configured to measure voltage and current of the current signals/pulses and to measure impedance rates using the measured voltage;

a plurality of electrodes in communication with the voltage-to-current convertor, one electrode of the plurality of electrodes configured to locate in the ear canal and another electrode of the plurality of electrodes configured to be located on the skin around the skull of a patient, performing the auditory processing evaluation by applying the current signals/pulses to the ear canal and skull of the patient in different waveforms at various frequency ranges and conveyed via the plurality of electrodes and examining the auditory pathway by applying the current signals/pulses, adjusted by the digital to analog converter controlled by the processor, through the electrodes located in the ear canal and on the skull;

one or more isolated channels, each channel including two or more additional electrodes;

wherein the transtympanic stimulator is configured to display the impedance rate between the electrodes in both channels via connection to the computing device's display, displaying an error message when the impedance rates are exceeded;

the computing device as part of the electrical transtympanic stimulator for further adjusting the parameters of the current signals/pulses and the computing device analyzing the auditory processing evaluation, wherein parameters include current, voltage, and frequency; and a protection circuit configured to disconnect the power supply from the plurality of electrodes when the current signals/pulses value exceeds the reference threshold value as measured by the voltage and current measurement module.

10. The electrical transtympanic stimulator of claim 9, wherein the computing device is at least any one of a smartphone, a laptop, a computer, and a tablet.

11. The electrical transtympanic stimulator of claim 10, further comprising an analog-to-digital converter, wherein the analog-to-digital converter is in communication with the processor and is configured to convert the current and voltage as measured by the voltage and current measurement module into a digital number representing the magnitude of the sampled current and voltage, respectively, thereby monitoring the current signals/pules applied to the patient and increasing patient's safety.

12. The electrical transtympanic stimulator of claim 9, wherein the frequency range can comprise any value within the range of 20 Hz to 20 kHz.

13. The electrical transtympanic stimulator of claim 9, further comprising a secondary protection circuit, further comprising an analog comparator and a secondary protection circuit, the analog comparator configured to compare the measure value of the current signals/pulses with the reference threshold value, wherein the secondary protection circuit disconnects the power supply when the compared value of the current signals/pulses exceeds the reference threshold value.

14. The electrical transtympanic stimulator of claim 9, wherein the amplifier is configured to amplify the analogue voltage signals that are produced by the digital-to-analog converter.

* * * * *